(12) United States Patent
Young et al.

(10) Patent No.: US 6,941,947 B2
(45) Date of Patent: Sep. 13, 2005

(54) UNIT DOSE DRY POWDER INHALER

(75) Inventors: Matthew E. Young, Cambridge (GB);
Stuart Brian William Kay, Cambridge (GB); Neil R Harrison, Birmingham (GB)

(73) Assignee: Quadrant Technologies Limited, Nottingham (GB)

( * ) Notice: Subject to any disclaimer, the term of this patent is extended or adjusted under 35 U.S.C. 154(b) by 11 days.

(21) Appl. No.: 10/322,867

(22) Filed: Dec. 18, 2002

(65) Prior Publication Data

US 2004/0118399 A1 Jun. 24, 2004

(51) Int. Cl.⁷ ............................................. A61M 15/00
(52) U.S. Cl. ......................... 128/203.21; 128/203.15; 128/200.14
(58) Field of Search ................ 128/200.14, 203.15, 128/203.21, 203.23, 200.23; 206/469, 438, 530, 531, 532

(56) References Cited

U.S. PATENT DOCUMENTS

| | | | |
|---|---|---|---|
| 4,210,140 A | | 7/1980 | James et al. |
| 4,778,054 A | | 10/1988 | Newell et al. |
| 4,811,731 A | * | 3/1989 | Newell et al. ......... 128/203.15 |
| 5,035,237 A | * | 7/1991 | Newell et al. ......... 128/203.15 |
| 5,207,217 A | * | 5/1993 | Cocozza et al. ....... 128/203.21 |
| 5,622,166 A | * | 4/1997 | Eisele et al. ........... 128/203.12 |
| 5,645,051 A | | 7/1997 | Schultz et al. |
| 5,881,719 A | * | 3/1999 | Gottenauer et al. .... 128/203.15 |
| 6,029,663 A | * | 2/2000 | Eisele et al. ........... 128/203.21 |
| 6,065,472 A | * | 5/2000 | Anderson et al. ...... 128/203.21 |
| 6,098,619 A | | 8/2000 | Britto et al. |
| 6,116,238 A | | 9/2000 | Jackson et al. |
| 6,367,473 B1 | * | 4/2002 | Kafer .................... 128/203.21 |
| 6,427,688 B1 | | 8/2002 | Ligotke et al. |
| 6,443,152 B1 | * | 9/2002 | Lockhart et al. ....... 128/203.21 |
| 6,604,522 B2 | * | 8/2003 | Arvidsson et al. ..... 128/203.15 |
| 2002/0040713 A1 | | 4/2002 | Eisele et al. |

FOREIGN PATENT DOCUMENTS

| | | |
|---|---|---|
| WO | WO 01/26720 A1 | 4/2001 |
| WO | WO01/72605 A1 | 10/2001 |

* cited by examiner

Primary Examiner—Glenn K. Dawson
Assistant Examiner—Darwin P Erezo
(74) Attorney, Agent, or Firm—Perkins Coie LLP (57) ABSTRACT

A unit dose dry powder inhaler has a dispersion chamber, optionally including one or more beads. A blister is supported adjacent to the dispersion chamber. A mouthpiece cover is removable from a mouthpiece, with movement of the mouthpiece cover causing the blister to open. An air flow path extends past or under the blister and into the dispersion chamber. As a result, the blister remains sealed until the inhaler is ready for use. The blister is then automatically opened when the mouthpiece cover is removed from the mouthpiece. Pharmaceutical dry powder is released from the blister and entrained in air flow through the inhaler, when the user inhales on the mouthpiece. The powder is dispersed in air within the dispersion chamber.

12 Claims, 10 Drawing Sheets

UNIT DOSE DRY POWDER INHALER

FIELD OF THE INVENTION

The field of the invention is dry powder inhalers.

BACKGROUND OF THE INVENTION

Inhalers are used to deliver drugs into a patient's lungs. Typically, an inhaler contains or provides a mixture of drug particles and air or propellant gas. The mixture is delivered via the patient inhaling from a mouthpiece on the inhaler with the air carrying the drug particles into the patient's lungs.

In dry powder inhalers, the drug particles, in the form of a fine dry powder, are entrained into an airflow, and inhaled by the patient, for treatment for various conditions, for example, bronchial asthma. Drugs delivered via a dry powder inhaler can be used to treat many conditions, including those unrelated to lung conditions, via the systemic absorption of the drug into the bloodstream, via the lung.

For effective dose delivery using a dry powder inhaler, the powder particles must first be dispersed to form a powder/air aerosol. Various techniques for forming powder aerosols have been proposed. One advantageous technique is described in U.S. Pat. No. 6,427,688 and International Application No. PCT/US01/03248, both incorporated herein by reference.

While certain drugs, such as asthma drugs, may be taken several times daily, other drugs, including certain peptides or proteins, are typically taken less frequently. Due to the delay in using these types of drugs after they are removed from their packaging, providing a large number of doses within a single package is not desirable, as some doses may become unusable due to exposure to the environment. In addition, many drugs are susceptible to a short shelf life when removed from a foil storage pouch or other sealed container, even under nominal environmental conditions. These types of drugs must be used almost immediately after being exposed to the environment. Various other drugs are also most often taken only in a single or a few dose. These may include vaccines, antidotes, pain reducers, anti venoms, as well as many others. Unit dose inhalers are also useful for single dose treatments, non-chronic applications, controlled or very expensive drugs where large quantities of drug would not be acceptable, or for drugs where overdose or abuse would have serious consequences. Unit dose inhalers may also be advantageous for children where providing them with, a single dose only avoids the potential for overdosing.

Inhalation provides several advantages over other delivery techniques such as oral delivery via the mouth or intravenous delivery using a syringe. Inhalation is fast, patient friendly, non-invasive, and can provide rapid absorption into the body. While unit dose inhalers have been proposed in the past, they have met with only varying degrees of success due to performance or other factors. Accordingly, there is a need for an improved unit or single dose inhaler for efficiently providing a prepackaged single dose of a powdered drug.

SUMMARY OF THE INVENTION

In a first aspect, a unit dose dry powder inhaler has a dispersion chamber, optionally including one or more beads. A blister is supported adjacent to the dispersion chamber. A mouthpiece cover is removable from a mouthpiece, with movement of the mouthpiece cover causing the blister to tear or shear open. An air flow path extends past or under the blister and into the dispersion chamber. The blister remains sealed until the inhaler is ready for use. The blister is then automatically opened when the mouthpiece cover is removed from the mouthpiece. Pharmaceutical dry powder is released from the blister and entrained in air flow through the inhaler, when the user inhales on the mouthpiece. The powder is dispersed in air within the dispersion chamber and forms an aerosol inhaled by the user.

In a second aspect, the blister is formed with a first or top layer and a second or bottom layer. A blister post is attached to at least a portion of the bottom layer. As the mouthpiece cover moves to an open position, the blister post moves away from the blister, shearing out the bottom layer, releasing the dry powder, and forming an air flow path through or by the blister. Hold up of powder within the blister is reduced, thereby more reliably providing a full unit dose to the user.

In a third and separate aspect, a blister is adhered over an air inlet in a chamber front or top section. A chamber back or bottom section has a top or first plate attached to the chamber front, and a bottom or second piece, including the blister post. In the closed position, a dust cap covers a mouthpiece on the chamber front section. As the dust cap is removed from the mouthpiece, the blister post is moved away from the chamber front section and the blister, tearing or shearing out the bottom layer of the blister, and releasing the powder contents of the blister for inhalation.

Other objects, features, and advantages will appear from the following detailed description.

The invention resides as well in subcombinations of the features and steps shown and described.

It is an object of the invention to provide an improved unit dose dry powder inhaler.

BRIEF DESCRIPTION OF THE DRAWINGS

In the drawings, wherein the same reference number indicates the same element, in each of the views:

FIG. 1 is a top perspective view of the present unit dose dry powder inhaler, in the closed or storage position.

FIG. 2 is a bottom perspective view of the inhaler shown in FIG. 1.

FIG. 3 is a top perspective view of the dust cap or mouthpiece cover shown in FIG. 1, before assembly.

FIG. 4 is a bottom or rear perspective view of the chamber back section shown in FIGS. 1 and 2, with the back chamber assembly shown in an unfolded or unassembled condition, for purpose of illustration.

FIG. 5 is a top or front view of the chamber back section shown in FIG. 4.

FIG. 6 is a top perspective view showing the first and second plates forming the chamber back section being moved together for manufacture of the inhaler.

FIG. 7 is a top perspective view showing the chamber back section of FIGS. 4–6 in a fully pre-assembled component.

FIG. 8 is a top perspective view of the chamber front section.

FIG. 9 is a bottom or rear perspective view of the chamber front section shown in FIG. 8.

FIG. 10 is a top perspective view of the chamber back section shown in FIGS. 4–7 joined to or assembled with the chamber front section shown in FIGS. 8 and 9, to form a chamber assembly.

DETAILED DESCRIPTION OF THE DRAWINGS

Figure 1:
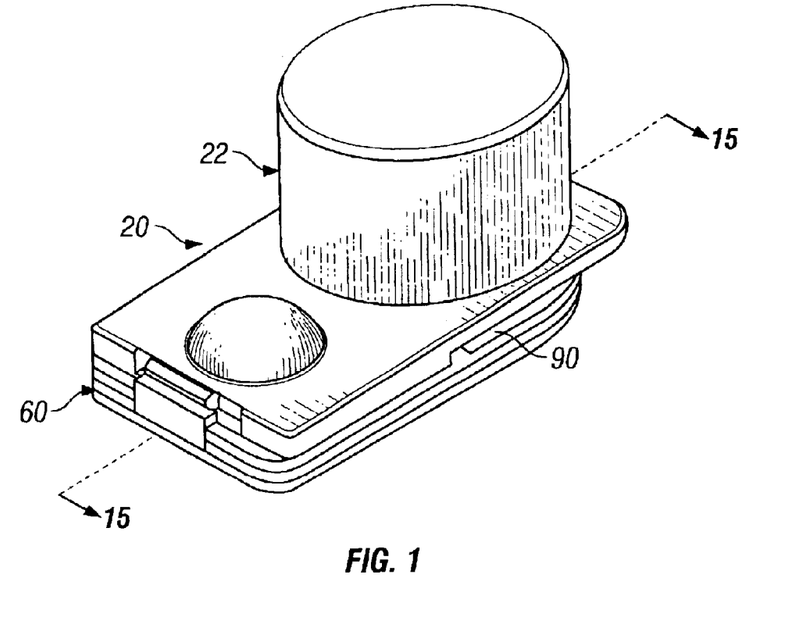
Figure 2:
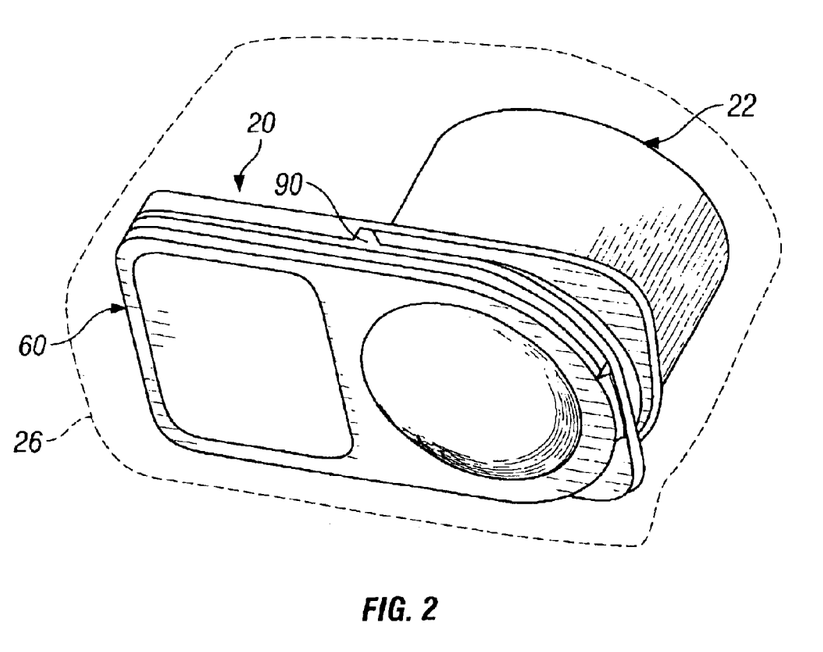

Turning now to the drawings, as shown in FIGS. 1, 2, 13 and 14, a unit dose inhaler 20 includes a back section 60 attached to a front section 90 which is covered by a dust cap 22. FIGS. 1 and 2 show the inhaler 20 in the closed or storage position. The inhaler 20 as shown in FIG. 2 may optionally be enclosed within a sealed pouch, overwrapper or container 26.

Figure 3:
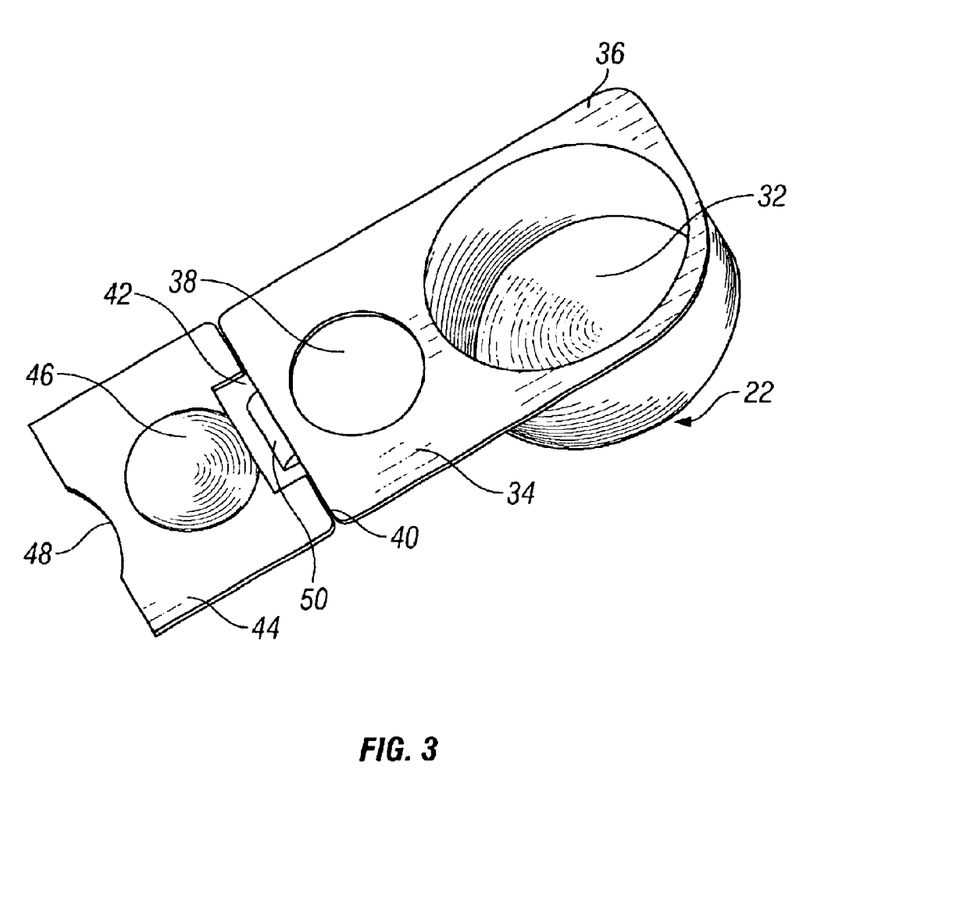

FIG. 3 shows the dust cap 22 as a separate component, before assembly into the inhaler of FIGS. 1 and 2. As shown in FIG. 3, the dust cap 22 includes a generally cylindrical cap section 32 formed in a base plate 34. A shield plate 44 is connected to the base plate 34 by a flex joint or hinge 40. An actuating tab or tooth 50 extends into a hinge slot 42 in the shield plate 44 at the flex or hinge joint 40. A blister shield dome 46 is formed in the shield plate 44 between the hinge slot 42 and an edge cut-out 48. The shield dome 46 protrudes upwardly in the opposite direction of cap section 32, as shown in FIG. 3, which shows the bottom surface of the dust cap 22 in its unassembled position. A clearance hole 38 is located in the base plate 34, so that when the shield plate 44 is folded over against the base plate 34, as shown in FIG. 1, the blister shield dome 46 is aligned within and protrudes through the clearance hole 38. A lift tab 36 on the base plate 34 provides a finger grasping surface, for actuating the inhaler from the position shown in FIG. 1, to the position shown in FIG. 14.

The dust cap 22, as well as the front section 90 and back section 60, are preferably made from molded plastics materials, with all features molded in.

Figure 4:
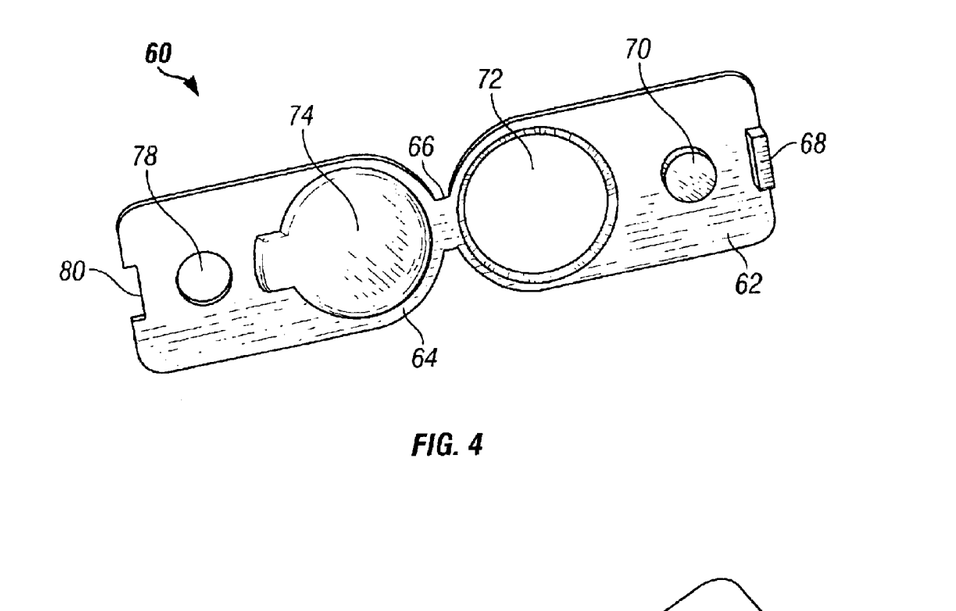
Figure 5:
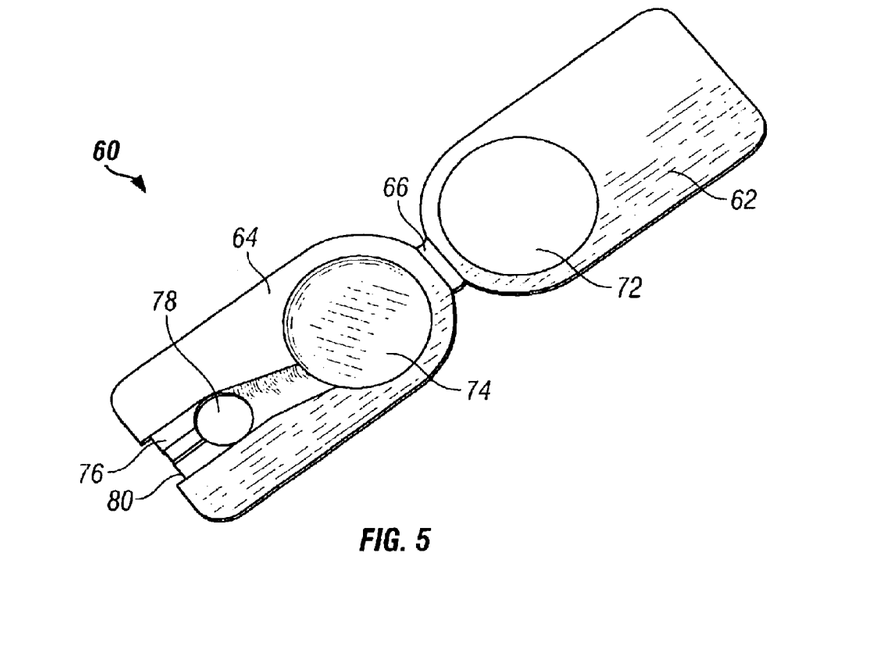

Turning now to FIGS. 4, 5, 6, and 7, the back section 60 includes a shear plate 62 attached to a chamber plate 64 by a flex joint or hinge 66. As shown in FIGS. 4 and 5, a plate tab 68 and blister post 70 extend downwardly from the shear plate 62. A chamber clearance hole 72 is provided in the shear plate 62 adjacent to the hinge 66. The chamber plate 64 has a notch 80 to provide clearance for the plate tab 68. Similarly, a blister post clearance hole 78 is provided in the chamber plate 64 to provide clearance for the blister post 70, when the shear plate 62 and chamber plate 64 are folded together to form the back section 60.

Figure 6:
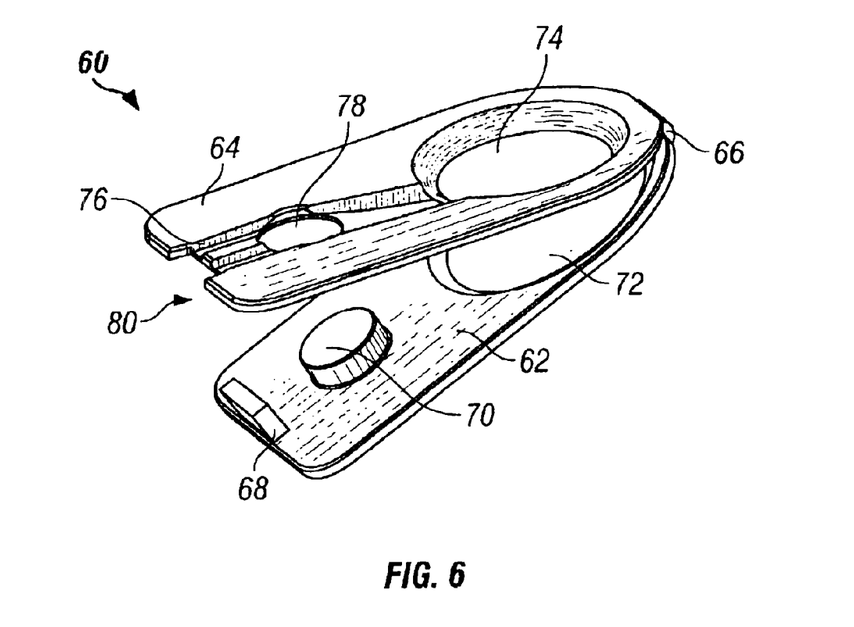
Figure 7:
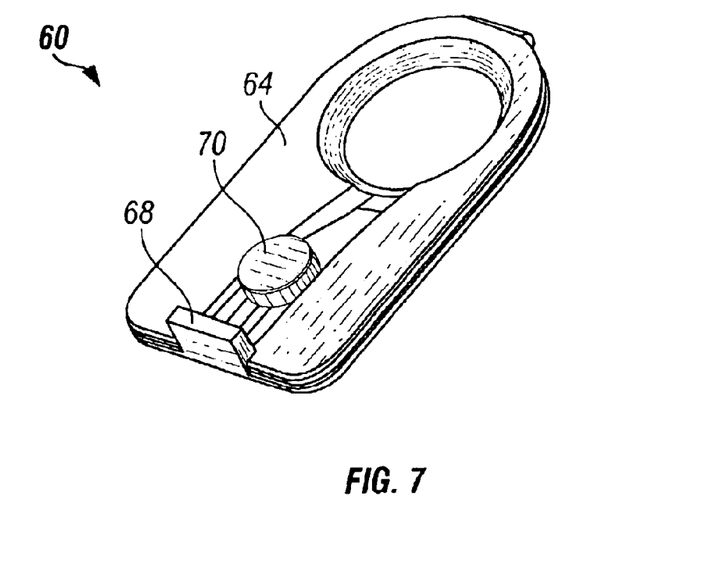

Referring still to FIGS. 4 and 5, a rear chamber wall 74 is formed in the chamber plate 64 adjacent to the hinge 66. A rear air inlet slot or passageway 76 in the chamber plate 64 extends from the tab slot 80, over the blister post clearance hole 78 and into the chamber rear wall 74, as best shown in FIG. 5. The back section 60 is assembled by folding the shear plate 62 and chamber plate 64 together, as shown in FIGS. 6 and 7. The plate tab 68 moves into the tab slot 80. The blister post 70 extends up through the blister post clearance hole 78. The chamber clearance hole 72 provides clearance for the rearward or downwardly projecting chamber rear wall 74.

As shown in FIG. 7, as preassembled, the shear plate 62 is substantially flush against the chamber plate 64. The plate tab 68 and slot 80 are dimensioned to provide a snap fit.

Figure 8:
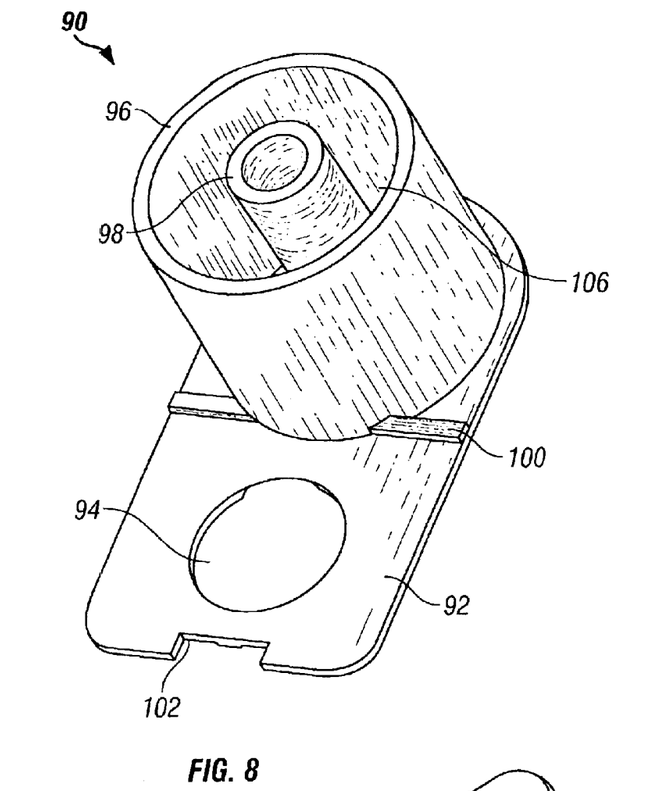
Figure 9:
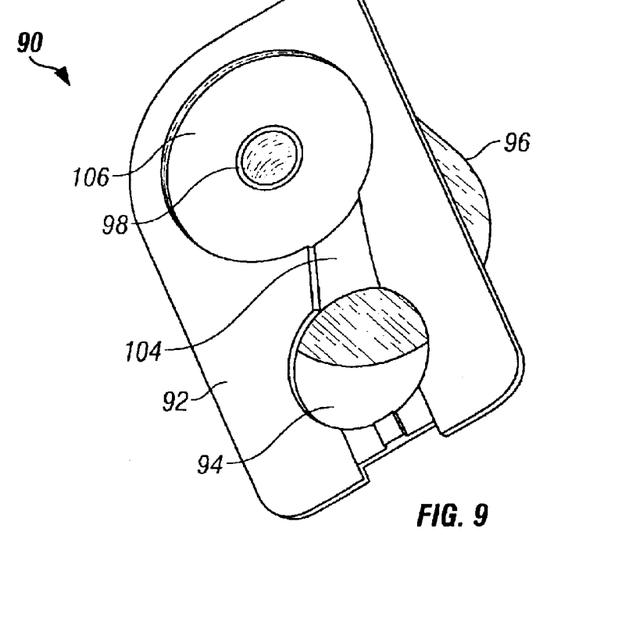

Turning to FIGS. 8 and 9, the front section 90 has a generally cylindrical mouthpiece 96 and chamber tube 98 extending upwardly and perpendicularly from a blister plate 92. A blister opening 94 is provided in the blister plate 92, to provide clearance for a blister. A blister plate tab slot 102 is provided at the top end of the blister plate 92, and is adapted to provide clearance for, and a snap fit with, the plate tap 68. A shield plate step 100 extends across the blister plate 92, to facilitate assembly of the components of the inhaler 20.

Referring to FIG. 9, a domed front chamber wall 106 is formed in the blister plate 92, concentric with the chamber tube 98. A front air inlet 104 extends from the blister plate tab slot 102 over the blister opening 94 and into the front chamber wall 106, similar to the complimentary features 76, 78, and 74 in the back section 60.

Figure 10:
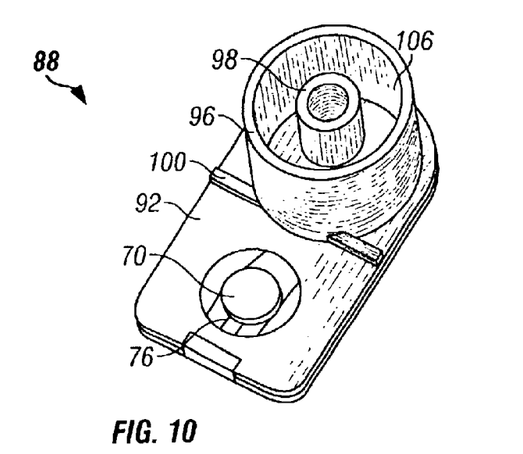

Referring to FIG. 10, the assembled back section 60, as shown in FIG. 7, is attached to the front section 90, via adhesives, sonic welding, snap fit, etc. As shown in FIG. 10, the back section 60 assembled with the front section 90, together form a dispersion or chamber assembly 88. The top surface of the chamber plate 64 is attached to the bottom surface of the blister plate 92. The chamber back wall 74 in the chamber plate 64 aligns and comes together with the chamber front wall 106 of the front section 90. The rear air inlet 80 on the chamber plate 64 aligns and comes together with the front air inlet 104 in the blister plate 92, connecting into the dispersion chamber 108 formed by the back and front chamber walls 74 and 106. The blister post 70 extends up through the blister opening 94 in the blister plate 92. The top surface of the blister post 70 is substantially level with the top surface of the blister plate 92. The annular clearance or spacing between the blister post 70 and the blister plate 92 surrounding it ranges from 1–10, 2–6, or 3–5 mm. This spacing allows the blister post to tear or shear out the bottom of the blister, without causing the blister to crush in or extensively deform.

Figure 11:
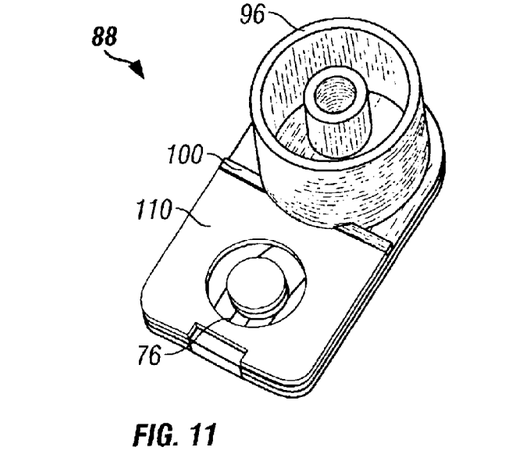
FIG. 11 is a top perspective view similar to FIG. 10, and showing adhesive applied to illustrate the manufacturing process.
Figure 12:
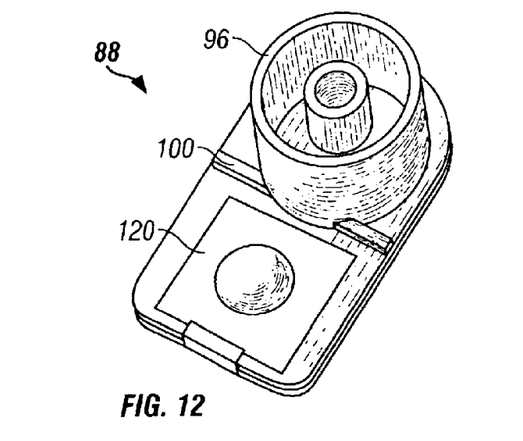
FIG. 12 is a top perspective view showing a blister adhered to the assembly of FIG. 11.

As shown in FIGS. 11 and 12, an adhesive is applied to the blister plate 92 around the blister opening 94. The adhesive 110 is also applied to the top surface of the blister post 70. A blister 120 is then adhered to the top surface of the blister plate 92, with the dome or hemispherical section of the blister extending upwardly (in the same direction as the mouthpiece 96). The blister 120 contains a dry pharmaceutical powder 126 sealed between a base layer 122 and a shear layer 124. These layers are typically metal foil and may include other layers as well. Various blisters may be used as described, for example, in U.S. Pat. No. 4,778,054, incorporated herein by reference.

Figure 13:
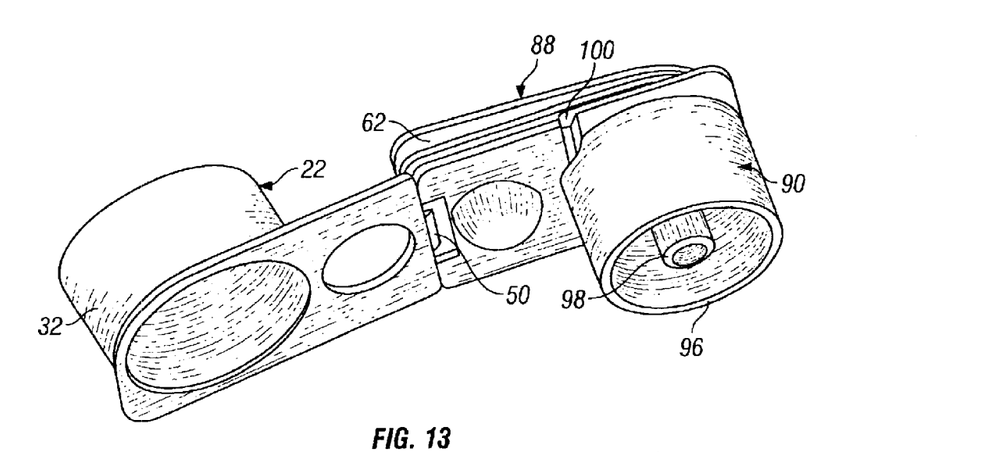
FIG. 13 is a top perspective view of the fully assembled unit dose dry powder inhaler, in the open position, with the dust cap of FIG. 3 attached to the dispersion chamber assembly shown in FIG. 12.
Figure 14:
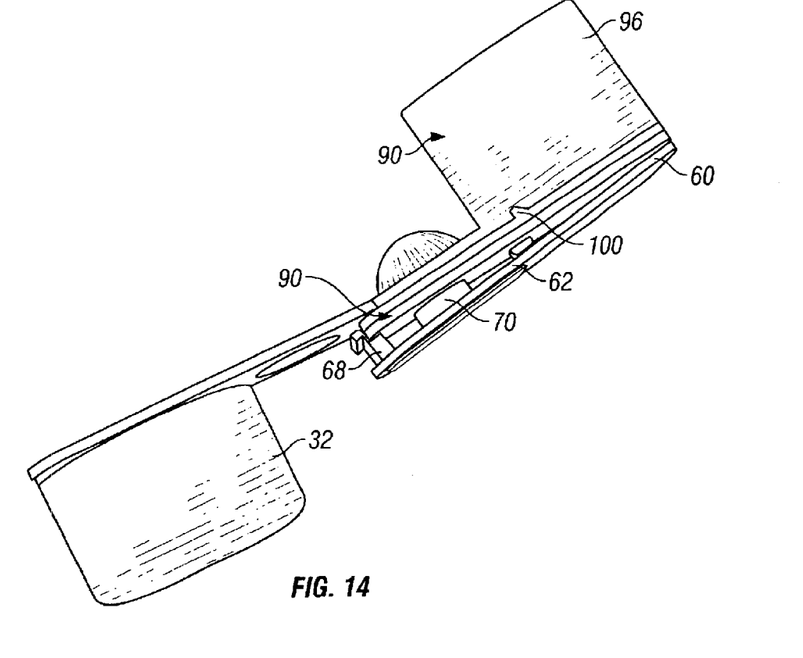
FIG. 14 is a bottom and side perspective view of the inhaler shown in FIG. 13.

Referring to FIG. 13, the dustcap 22 is then assembled to the chamber assembly 88. Specifically, the shield plate 44 is placed over the blister 120, with the outer edges of the shield plate 44 in contact with the adhesive 110. This step is performed with the shield plate 44 folded over at the flex joint 40, so that the shield plate 44 is in contact with the base plate 34. With the completion of this step, the inhaler 20 is fully assembled, as shown in FIGS. 1 and 2. The inhaler 20 may then be placed into a sealed envelope or overwrap 26.

Figure 15:
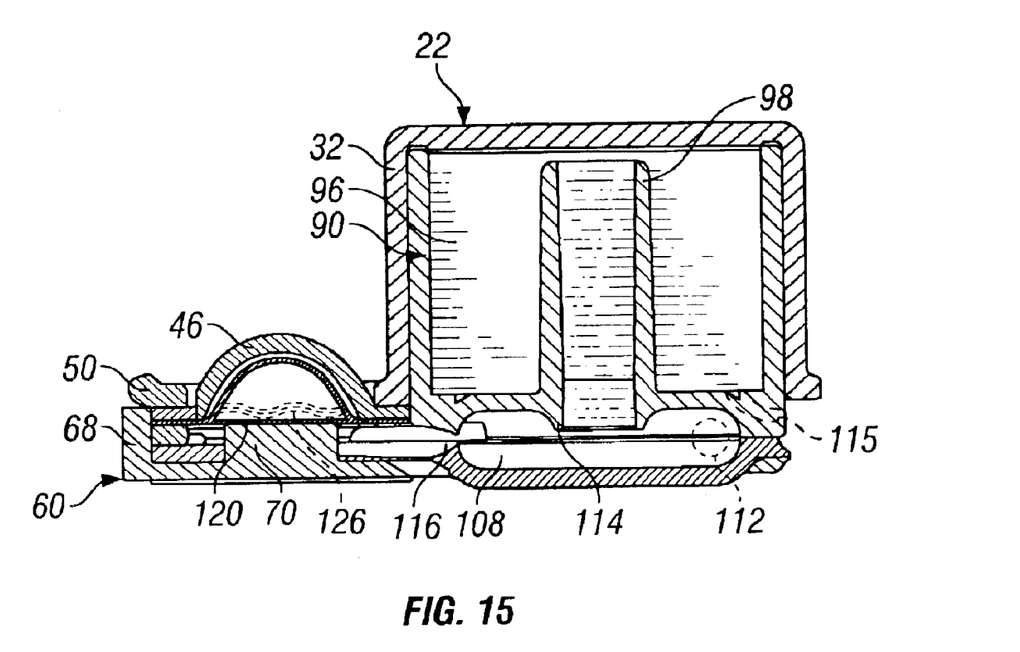
FIG. 15 is a section view taken along line 15—15 of FIG. 1, and showing the inhaler in the closed position.

The dispersion chamber 108 formed by bringing together the chamber back wall 74 of the back section 60 and the chamber front wall 106 of the front section 90 has an inner rim 114 at the bottom end of the chamber tube 98 as shown in FIG. 15. One or more beads 112 are captive within the dispersion chamber 108, as described in U.S. patent application Ser. No. 09/773,261 incorporated herein by reference. The rear air inlet 76 and the front air inlet 104 together form a chamber inlet 116, extending from the top end of the inhaler 20 (at the slots 80 and 102), extending over (and/or around) the blister post 70 and into the dispersion chamber 108. One or more sheath air openings 115 may optionally be provided through the mouthpiece 96.

In use, as shown in FIGS. 1, 2, and 15, the dust cap 22 is in place over the mouthpiece 96. The pharmaceutical dry powder 126 is sealed within the blister 120. The blister 120 is enclosed on top by the shield dome 46 and by the shear plate 62 below, to better avoid physical damage to the blister 120 during storage and handling. The beads 112 are placed within the dispersion chamber 108 before the back section 60 and front section 90 are joined together. The inner rim 114 prevents the beads 112 from moving out of the dispersion chamber 108 through the chamber tube 98.

Figure 16:
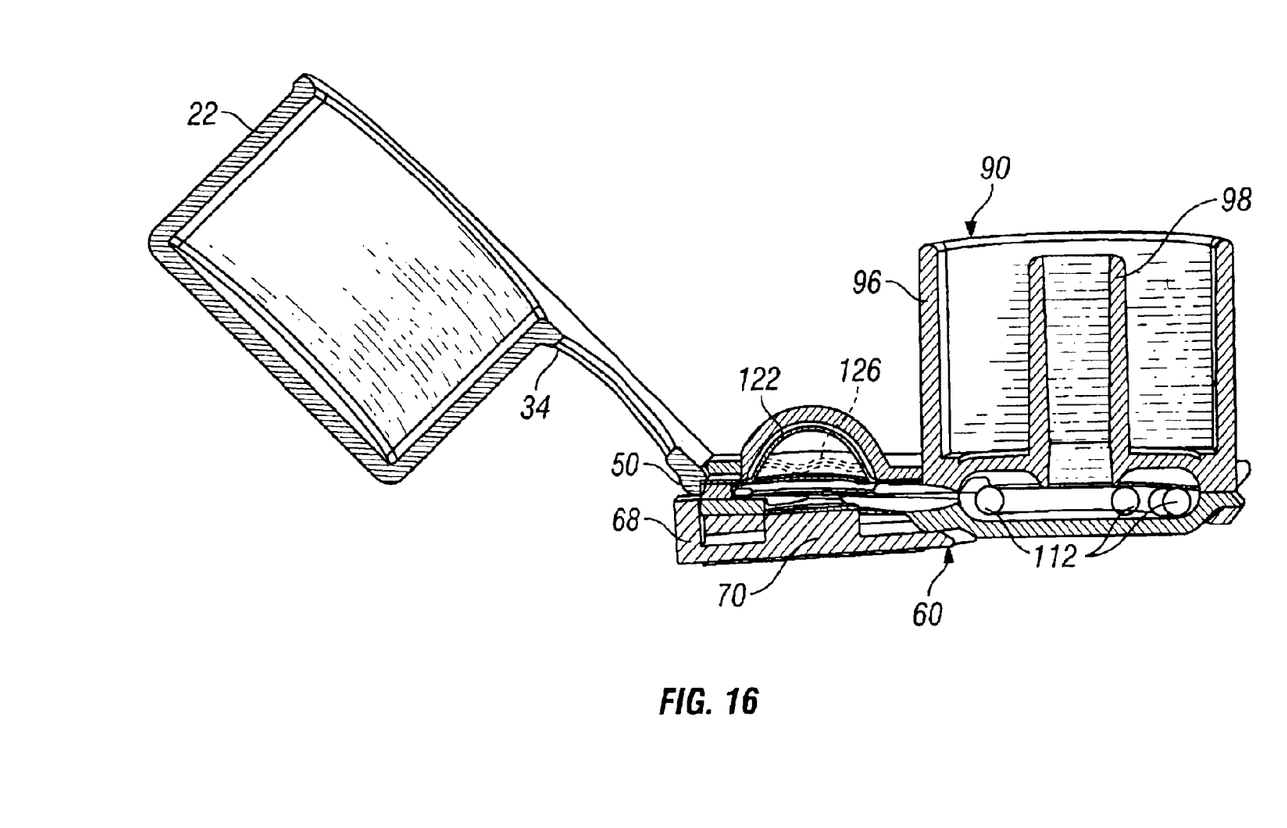
FIG. 16 is a section view similar to FIG. 15, and showing the inhaler in the open position.

The user lifts up on the lift tab 36, pivoting the base plate 34 from the closed position shown in FIG. 15, to the open position shown in FIG. 16. This removes the cap section 32 from the mouthpiece 96.

Figure 17:
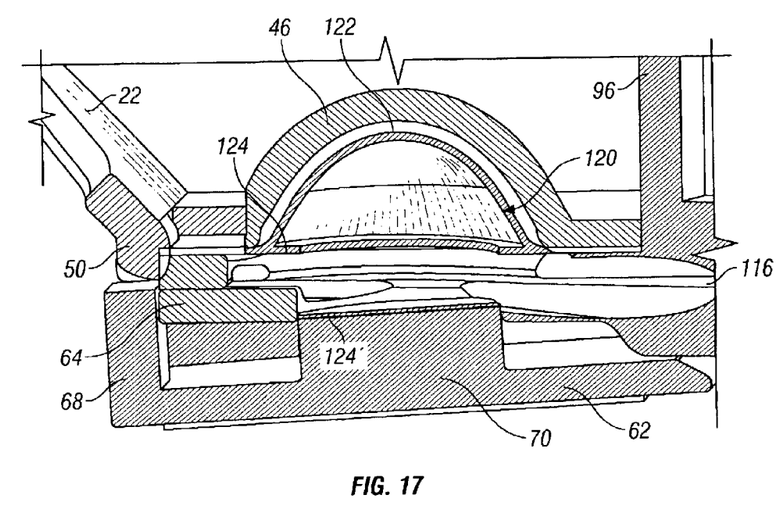
FIG. 17 is an enlarged detail view of the blister and inhaler components shown in FIG. 16.

Referring to FIGS. 15, 16, and 17, as the base plate 34 is pivoted to the open position, the tab tooth 50 pushes down on the plate tab 68, with a cam-like movement. This drives the shear plate 62 downwardly. The blister post 70 moves down with the shear plate 62. As the shear layer 124 or bottom layer of the blister 120 is adhered to the blister post 70, the movement of the blister post 70 shears or tears out the shear layer 124 of the blister 120. As this occurs, some of the powder 126 in the blister 120 will move or fall out of the blister 120 into the air inlet or flow path 116. Some of the powder 126 remains on top of the now separated shear layer 124' shown in FIG. 17.

The user then places the mouthpiece 96 in the mouth and inhales. Air is drawn through the inlet 116 carrying the powder 126 into the chamber 108. The air inlet 116 extends into the chamber 108 on a chord or tangentially. The air drawn through the chamber 108 causes the beads 112 to circulate rapidly around in the chamber. This bead movement disperses and mixes the powder 126 with air. The air and powder then move out of the chamber 108 through the chamber tube 98, for inhalation by the user. Sheath or bleed air, if used, flows in through the openings 115 and moves generally parallel to the cylindrical side-walls of the mouthpiece 96. The sheath air helps to reduce deposition of powder particles in the mouth and throat allowing more of the particles to reach the lung.

While the inhaler 20 may be used in any orientation, the top end, at the plate tab 68, is preferably to the side, or above the mouthpiece 96, for better movement of powder 126 into the chamber 108. After use, the inhaler 20 may be collected for recycling, or it may be discarded.

Thus, a novel unit dose dry powder inhaler has been shown and described. Various changes and substitutions may of course be made, without departing from the spirit and scope of the invention. The invention, therefore, should not be limited, except by the following claims, and their equivalents.

What is claimed is:

1. An inhaler comprising:
    a dispersion chamber;
    a blister containing a pharmaceutical between a first layer and a second layer;
    a shear plate pivotably moveable relative to the blister;
    a post attached to the shear plate, and to at least a portion of the second layer, and with the post moveable with the shear plate in a direction away from the blister, to open the blister; and
    a mouth piece associated with the dispersion chamber and a mouthpiece cover pivotable relative to the shear plate for moving the post away from the blister to open the blister.

2. The inhaler of claim 1 with the mouthpiece cover having a cap section adapted to fit over the mouthpiece, a base plate, and a shield plate including a blister shield dome covering the first layer of the blister.

3. The inhaler of claim 1 with the mouthpiece including a chamber tube connecting into the dispersion chamber within a mouthpiece cylinder attached onto a blister plate.

4. The inhaler of claim 3 wherein an outer perimeter area of the second layer of the blister is attached to the blister plate.

5. The inhaler of claim 1 further including a chamber plate overlying the shear plate, and with the chamber plate including a post clearance hole around the blister post, a dispersion chamber back wall, and a back air inlet slot.

6. The inhaler of claim 5 with the mouthpiece including a dispersion chamber front wall, and with the dispersion chamber formed by the dispersion chamber back wall of the chamber plate joined with the dispersion chamber front wall of the mouthpiece.

7. The inhaler of claim 6 with the mouthpiece including a front air inlet slot, with the back air inlet slot of the chamber plate and the front air inlet slot of the mouthpiece forming an air inlet passing around the blister post and connecting into the dispersion chamber.

8. The inhaler of claim 5 with the shear plate attached to the chamber plate and further including plate tab engageable by the mouthpiece cover.

9. The inhaler of claim 8 further including a tab tooth on the mouthpiece cover engageable against the plate tab, a the mouthpiece cover is moved away from the mouthpiece, to drive the post on the shear plate away from the blister plate to open the blister.

10. The inhaler of claim 9 with a first end of the shear plate attached to a first end of the chamber plate, and with the plate tab on a second end of the chamber plate opposite the first end thereof, with the second end of the chamber plate moveable away from the chamber plate an the blister, upon engagement of the plate tab by the tab tooth of the mouthpiece cover.

11. A dry powder inhaler comprising:
    a mouthpiece;
    a blister supported on the mouthpiece;
    a mouthpiece cover,
    means for opening the blister by removing the mouthpiece cover from the mouthpiece.

12. A method for delivering a unit dose of a dry powder pharmaceutical, comprising the steps of:
    pivoting a mouthpiece cover away from a mouthpiece of an inhaler;
    moving a blister post adhered to a portion of the blister away from the blister with the pivoting movement of the mouthpiece;
    shearing open the blister via the blister post;
    allowing at least some of a dry powder pharmaceutical in the blister to deposit into an air passageway leading into a dispersion chamber;
    drawing air through the dispersion chamber and air passageway and out through the mouthpiece.

* * * * *